US012651658B2

(12) United States Patent
Hebebrand et al.

(10) Patent No.: US 12,651,658 B2
(45) Date of Patent: Jun. 9, 2026

(54) METHODS FOR TREATING ANOREXIA NERVOSA AND RELATED CONDITIONS BY ADMINISTERING A LEPTIN RECEPTOR AGONIST

(71) Applicant: Universität Duisburg-Essen, Essen (DE)

(72) Inventors: Johannes Hebebrand, Essen (DE); Jochen Antel, Essen (DE); Gabriella Milos, Zürich (CH)

(73) Assignee: UNIVERSITÄT DUISBURG-ESSEN, Essen (DE)

( * ) Notice: Subject to any disclaimer, the term of this patent is extended or adjusted under 35 U.S.C. 154(b) by 872 days.

(21) Appl. No.: 17/822,019

(22) Filed: Aug. 24, 2022

(65) Prior Publication Data

US 2023/0080196 A1     Mar. 16, 2023

Related U.S. Application Data

(60) Provisional application No. 63/237,189, filed on Aug. 26, 2021.

(51) Int. Cl.
| | |
|---|---|
| *G16H 20/10* | (2018.01) |
| *A61K 38/22* | (2006.01) |
| *G16H 20/70* | (2018.01) |

(52) U.S. Cl.
CPC ......... *G16H 20/10* (2018.01); *A61K 38/2264* (2013.01); *G16H 20/70* (2018.01)

(58) Field of Classification Search
None
See application file for complete search history.

(56) References Cited

PUBLICATIONS

Exner et al., Leptin suppresses semi-starvation induced hyperactivity in rats: implications for anorexia nervosa. Mol. Psychiatry (2000), 5, p. 476-481.*
Pipke, et al., Starvation induced hyperactivity in the rat: the role of endocrine and neurotransmitter changes. Neuroscience and Biobehavioral Reviews (1993), 17, p. 287-294.*
Welt, et al. Recombinant human leptin in women with hypothalamic amenorrhea. New England Journal of Medicine (2004), 351:10, p. 987-997.*
Depression and eating disorders. Eating Disorder Hope. Apr. 17, 2021. Internet—Wayback Machine. p. 1-4.*
Hebebrand J, Bulik CM, "Critical appraisal of the provisional DSM-5 criteria for anorexia nervosa and an alternative proposal", Int J Eat Disord 2010 (14 pages).
Hlebebrand et al, "Clinical Trials Required to Assess Potential Benefits and Side Effects of Treatment of Patients With Anorexia Nervosa With Recombinant Human Leptin", Front Psychol. vol. 10, art. 769, 2019 (23 pages).

(Continued)

*Primary Examiner* — Joanne Hama
*Assistant Examiner* — Jami Michelle Gurley
(74) *Attorney, Agent, or Firm* — Merchant & Gould P.C.

(57) ABSTRACT

The invention concerns methods for treating unwanted body weight loss, and/or medically undesired body weight loss, or eating disorders (such as anorexia nervosa), by administration of a leptin receptor agonist, such as metreleptin. The invention also relates to methods for increasing body weight in a subject in need of the treatment.

15 Claims, 8 Drawing Sheets

Patient A

DOSING PERIOD

1 ——— Repetitive Thoughts of Food ——— Fear of Weight Gain 4
2 ——— Drive for Activity          ——— Inner Tension     5
3 ——— Feeling Fat                 ——— Depressed Mood    6

(56)                    References Cited

PUBLICATIONS

Hebebrand et al., "Leptin levels in patients with anorexia nervosa are reduced in the acute stage and elevated upon short-term weight restoration", Mol. Psychiatry, 2, pp. 330-334, 1997.

Ahima RS, Flier JS, "Leptin", Annu. Rev. Physiol., 62, pp. 413-437, 2000.

Exner et al., "Leptin suppresses semi-starvation induced hyperactivity in rats: implications for anorexia nervosa", Mol. Psychiatry, 5, pp. 476-481. 2000.

Fernandes et al. "Leptin Suppresses the Rewarding Effects of Running via STAT3 Signaling in Dopamine Neurons", Cell Metab., 22: pp. 741-749, 2015.

Coccurello et al., Hedonic Eating and the 'Delicious Circle': From Lipid-Derived Mediators to Brain Dopamine and Back, Front. Neurosci., vol. 12, art. 271. 2018 (20 pages).

Monteleone et al., "Neuroendocrinology and brain imaging of reward in eating disorders: A possible key to the treatment of anorexia nervosa and bulimia nervosa", Prog. Neuropsychopharmacol. Biol. Psychiatry, 80, pp. 132-142, 2018.

Khanh, "Leptin and insulin signaling in dopaminergic neurons: relationship between energy balance and reward system", Front. Psychol., vol. 5, art. 846, 2014 (7 pages).

Brown et al. "Long-term effectiveness and safety of metreleptin in the treatment of patients with generalized lipodystrophy", Endocrine 60 (3), pp. 479-489, 2018.

FDA, "Summary Review for Regulatory Action", Myalept; Application No. 125390Orig1s000, ed. C.F.D.E.A. Research. In: Administration FaD, ed. Silver Spring, MD: FDA; 2014, (24 pages).

Farooqi et al. "Effects of recombinant leptin therapy in a child with congenital leptin deficiency", N Engl. J. Med., vol. No. 341, pp. 879-884, 1999.

Wabitsch et al. "Biologically inactive leptin and early-onset extreme obesity", N. Engl. J. Med ., 372, 1, pp. 48-54, 2015.

Paz-Filho G, Wong ML, Licinio J. Ten years of leptin replacement therapy. Obes Rev 2011;12:e315-23.

Welt et al., "Recombinant human leptin in women with hypothalamic amenorrhea". N. Engl. J. Med., 351, 10, pp. 987-997, 2004.

Chou et al. "Leptin is an effective treatment for hypothalamic amenorrhea", Proc .Natl. Acad. Sci. U S A, vol. 108, No. 16, pp. 6585-6590, 2011.

Sienkiewicz et al. "Long-term metreleptin treatment increases bone mineral density and content at the lumbar spine of lean hypoleptinemic women", Metabolism, 60, pp. 1211-1221, 2011.

Parsa-Parsi et al., "Reconsidering the Declaration of Helsinki", Lancet; 382, pp. 1246-1247, 2011.

WMA. "WMA Declaration of Helsinki—Ethical Principles for Medical Research Involving Human Subjects", Fortaleza, Brazil: 64th WMA General Assembly; 2013. (4 pages).

Hamilton M., "A rating scale for depression", J. Neurol. Neurosurg. Psychiatry, 23, pp. 56-62, 1960.

Beck AT, Steer RA, eds. Beck Depression Inventory—Manual. San Antonio: The Psychological Corporation1987 (4 pages).

Fantuzzi, "Leptin in the regulation of immunity, inflammation, and hematopoiesis", J. Leukoc. Biol., vol. 68, pp. 437-446, 2000.

Poeggeler et al. "Leptin and the skin: a new frontier", Exp. Dermatol., 19, pp. 12-18, 2010.

Yarandi et al., "Diverse roles of leptin in the gastrointestinal tract: modulation of motility, absorption, growth, and inflammation", 27 (3), 269-75, 2011 (14 pages).

Auyeung et al., "Prenatal and postnatal hormone effects on the human brain and cognition", Pflugers Arch., 465, pp. 557-571. 2013.

Milos et al., "Short-term metreleptin treatment of patients with anorexia nervosa: rapid on-set of beneficial cognitive, emotional, and behavioral effects", Translational Psychiatry vol. 10 No. 303, 10 pages (2020).

Thiel, A., Jacobi, C., Horstmann, S., Paul, T., Nutzinger, D.O., and Schüßler, G. (1997). Eine deutschsprachige Version des Eating Disorder Inventory EDI-2. PPmP—Psychotherapie • Psychosomatik • Medizinische Psychologie. 47 (1997) 365-376. (13 pages).

Ahima RS, Kelly J, Elmquist JK, Flier JS. Distinct physiologic and neuronal responses to decreased leptin and mild hyperleptinemia. Endocrinology. Nov. 1999; 140(11):4923-31. doi: 10.1210/endo. 140.11.7105. PMID: 10537115.

Casper RC. Restlessness and an Increased Urge to Move (Drive for Activity) in Anorexia Nervosa May Strengthen Personal Motivation to Maintain Caloric Restriction and May Augment Body Awareness and Proprioception: A Lesson From Leptin Administration in Anorexia Nervosa. Frontiers in Psychology. Jul. 25, 2022; 13:885274. doi: 10.3389/fpsyg.2022.885274. PMID: 35959022; PMCID: PMC9359127.

Cowley, et al. Leptin Activates Anorexigenic POMC Neurons through a Neural Network in the Arcuate Nucleus. George Fox University Faculty Publications—Department of Biology and Chemistry. 2001; 480-484.

Eli Lilly clinical trial. A Study of Tirzepatide (LY3298176) Plus Mibavademab Compared With Tirzepatide Alone in Adult Participants With Obesity. ClinicalTrials.gov. NCT06373146. 2026.

Figge-Schlensok, et al. A lateral hypothalamic neuronal population expressing leptin receptors counteracts anxiety to enable adaptive behavioral responses. Nature Neuroscience. Oct. 20, 2025; 2262-2272.

Friedman, et. al. Positional cloning of the mouse obese gene and its human homologue. Dec. 1, 1994; 372(6505):425-32. doi: 10.1038/372425a0.

Keys, et al. The biology of human starvation. University of Minnesota. vol. II, Chapter 36. 1950; 767-782.

Obradovic, et al. Leptin and Obesity: Role and Clinical Implication. Frontiers in Endocrinology. May 18, 2021; doi: 10.3389/fendo.2021. 585887.

Perakakis and Mantzoros. Evidence from clinical studies of leptin: current and future clinical applications in humans. Elsevier. vol. 161, 156053. Oct. 2024.

Scharner & Stengel. Animal Models for Anorexia Nervosa—A Systematic Review. Frontiers in Human Neuroscience. vol. 14, 596381. Jan. 20, 2021.

Spadini et al. Activity-based anorexia animal model: a review of the main neurobiological findings. Journal of Eating Disorders. Oct. 2, 2021; 9(1):123. doi: 10.1186/s40337-021-00481-x. PMID: 34600568; PMCID: PMC8487535.

Thavaraputta, et al. Anorexia nervosa and adrenal hormones: a systematic review and meta-analysis. Eur J Endocrinol. Sep. 1, 2023; 189(3):S64-S73. doi: 10.1093/ejendo/lvad123. PMID: 37669399; PMCID: PMC10498414.

Uysal, et al. Could recombinant human leptin (metreleptin) be a new hope in the treatment of anorexia nervosa? Psychiatria Danubina. Dec. 2025; 37(4):508-509. PMID: 41570218.

Stengel, et. al. Leptin and Physical Activity in Adult Patients with Anorexia Nervosa: Failure to Demonstrate a Simple Linear Association. Nutrients. Nov. 3, 2017; 9:1210.

* cited by examiner

Patient A

1 ——Repetitive Thoughts of Food ——Fear of Weight Gain 4

2 ——Drive for Activity          ——Inner Tension      5

3 ——Feeling Fat               ——Depressed Mood    6

Patient C

Patient A

Patient C

1 —— Testosterone (nmol/l)

2 —— bioavailable Testosterone (nmol/l)

3 —— LH (IU/l)

4 —— FSH (IU/l)

METHODS FOR TREATING ANOREXIA NERVOSA AND RELATED CONDITIONS BY ADMINISTERING A LEPTIN RECEPTOR AGONIST

FIELD OF THE INVENTION

The invention concerns methods for treating unwanted body weight loss or eating disorders (such as anorexia nervosa), by administration of a leptin receptor agonist, such as metreleptin. The invention also relates to methods for increasing body weight in a subject in need of the treatment.

DESCRIPTION

Anorexia nervosa (AN) is an eating disorder characterized by food restriction, odd eating habits or rituals, obsession with having a thin figure, and an irrational fear of weight gain. AN is often coupled with a distorted self-image, which may be maintained by various cognitive biases that alter how individuals evaluate and think about their bodies, food, and eating. Individuals with AN often view themselves as overweight or not thin enough even when they are severely underweight. While the majority of individuals with AN continue to feel hunger, they deny themselves all but very small quantities of food. AN has the highest mortality rate of any psychiatric illness.

Underweight, fear of weight gain, and body image disturbances represent cardinal features of AN[1]. Somatic and mental symptoms of this eating disorder are intertwined with those of starvation[2], which develops from prolonged energy restriction. Loss of fat mass in AN entails a drop in blood levels of the adipocyte-derived hormone leptin[3]. Ensuing hypoleptinemia represents a key endocrine feature of this eating disorder[2,4] and acts as the major signal for the adaptation to starvation[5]. Amenorrhea, hematological alterations, depressed mood, inflexibility, and repetitive thoughts of food represent clinically relevant examples of starvation related symptoms, which might be triggered or worsened by hypoleptinemia[3]. Rodent and human studies also suggest a link between hyperactivity and low circulating leptin levels[6]. In rats, semi-starvation induced hyperactivity is rapidly amenable to treatment with recombinant leptin[6]. In light of the potential involvement of the reward system in AN, the role of leptin as a strong modulator of the reward system deserves notice[3,7-10].

The current standard of care, based on AN's high comorbidity with anxiety and depression, is to treat patients with psychotropic medications. Unfortunately, these pharmacological treatments have still not satisfactory impact on the restrictive eating behavior that is in part responsible for the high mortality rate of AN. Accordingly, there remains a need in the art for methods of treating anorexia nervosa that modulate the restrictive eating behaviors that drive AN's severe weight loss and high mortality rate.

BRIEF DESCRIPTION OF THE INVENTION

Generally, and by way of brief description, the main aspects of the present invention can be described as follows:

In a first aspect, the invention pertains to a method for treating a subject suffering from a neuropsychiatric condition associated with weight loss or underweight, preferably associated with underweight due to either weight loss or the failure to gain weight during development, comprising an administration of a therapeutically effective amount of leptin, or a leptin- and/or leptin receptor agonist, or a leptin analog or derivative thereof, to the subject and thereby ameliorating one or more conditions associated with (or associated with the cause of) weight loss or underweight in the subject.

In a second aspect, the invention pertains to a method for increasing body weight in a subject in need of the treatment, the method comprising a step of administering an effective amount of leptin, or a leptin- and/or leptin receptor agonist, or a leptin analog or derivative thereof, to the subject.

DETAILED DESCRIPTION OF THE INVENTION

Figure 1:
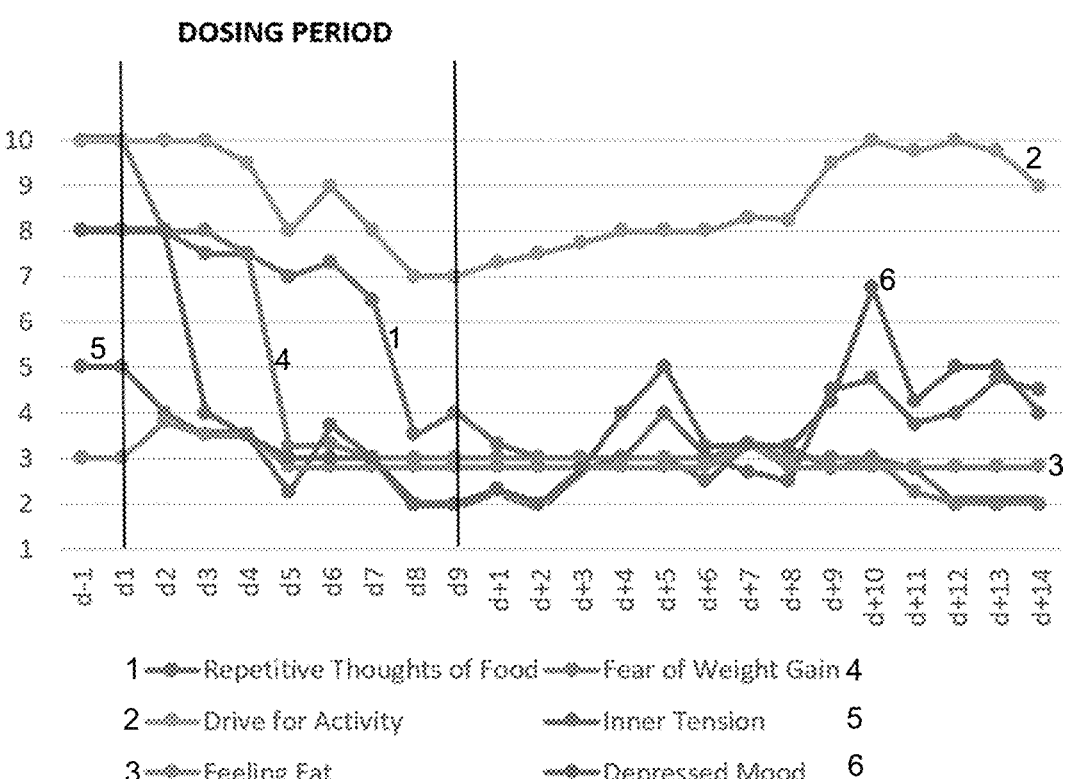
FIG. 1: shows VAS for key cognitions and emotions: Effects of short-term metreleptin treatment in patient A including follow-up observations for 14-days, showing means of (patient self-rated) six key cognitions and emotions assessed thrice daily with visual analog scales (range 1-10).

In the following, the elements of the invention will be described. These elements are listed with specific embodiments; however, it should be understood that they may be combined in any manner and in any number to create additional embodiments. The variously described examples and preferred embodiments should not be construed to limit the present invention to only the explicitly described embodiments. This description should be understood to support and encompass embodiments which combine two or more of the explicitly described embodiments or which combine the one or more of the explicitly described embodiments with any number of the disclosed and/or preferred elements. Furthermore, any permutations and combinations of all described elements in this application should be considered disclosed by the description of the present application unless the context indicates otherwise.

The present invention provides methods for treating or preventing unwanted weight loss and eating disorders, such as anorexia nervosa, and associated neuropsychiatric conditions by administering leptin receptor agonists.

In a first aspect, the invention pertains to a method for treating a subject suffering from a neuropsychiatric condition associated with weight loss or underweight or associated with underweight due to either weight loss or the failure to gain weight during development, comprising an administration of a therapeutically effective amount of leptin, or a leptin- and/or leptin receptor agonist, or a leptin analog or derivative thereof, to the subject and thereby ameliorating one or more conditions associated with (or associated with the cause of) weight loss or underweight in the subject.

As used herein, "treatment" is an approach for obtaining beneficial or desired clinical results. For purposes of this invention, beneficial or desired clinical results include, but are not limited to, one or more of the following: improving, lessening severity, alleviation of one or more symptoms associated with a disease. For example, for treatment of cachexia and/or unwanted weight loss, beneficial or desired clinical results include, but are not limited to, any improvement, lessening of severity, and/or alleviation of any one or more of the following: weight loss, lipolysis, loss of muscle and visceral protein, anorexia (i.e., loss of appetite), reduced food/caloric intake, chronic nausea, fatigue and weakness. For treatment of anorexia nervosa, beneficial or desired clinical results include, but are not limited to, any one or more of the following: improvement of appetite, attenuation of food resentment, gaining weight, maintaining normal nutritional status, hydration and electrolyte balance, maintaining normal body weight for age and height, reducing frequency and duration of hospitalization, and reducing risk of death.

"Ameliorating" a disease or one or more symptoms of the disease means a lessening or improvement of one or more symptoms associated with the disease as compared to not administering a leptin receptor agonist. "Ameliorating" also includes shortening or reduction in duration of a symptom.

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the outset of the disease, including biochemical, histological and/or behavioural symptoms of the disease, its complications and intermediate pathological phenotypes presenting during development of the disease, in particular as disclosed herein elsewhere. For therapeutic use, beneficial or desired results include clinical results such as reducing intensity, duration, or frequency of attack of the disease, and decreasing one or more symptoms resulting from the disease (biochemical, histological and/or behavioral), including its complications and intermediate pathological phenotypes presenting during development of the disease, increasing the quality of life of those suffering from the disease, decreasing the dose of other medications required to treat the disease, enhancing effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

The term "neuropsychiatric condition" as used herein refers to clinical problems of cognition and/or behavior caused by or associated with weight loss or underweight. Neuropsychiatric conditions include, but are not limited to, psychotic disorders, cognitive disorders, anxiety disorders, and attention disorders. In preferred embodiments of the methods of the invention, the neuropsychiatric condition is (typical) anorexia nervosa.

The term "Anorexia Nervosa" (AN) as used herein refers to a psychiatric disorder that may be characterized at least in part by a pathological level of extreme weight loss. According to the Diagnostic and Statistical Manual of Mental Disorders, 5th Ed., (DSM-5), diagnostic criteria for AN include: 1) restricting food intake—eating less than needed to maintain a body weight that's at or above the minimum normal weight for your age and height; 2) fear of gaining weight: intense fear of gaining weight or becoming fat, or persistent behavior that interferes with weight gain, such as vomiting or using laxatives, even though you're underweight; and 3) problems with body image: denying the seriousness of having a low body weight, connecting your weight to your self-worth, or having a distorted image of your appearance or shape.

The term "leptin receptor agonist" refers to a leptin protein, a fragment of a leptin protein having physiological properties of the leptin protein, analog (or variant) leptin protein or variant of a fragment of a leptin protein fragment, having physiological properties of the leptin protein, a leptin receptor agonist being a leptin mimic or any combinations thereof.

Such compounds may be the full (human) leptin protein having a sequence as shown in Zhang Y, Proenca R, Maffei M, Barone M, Leopold L, Friedman J M. Positional cloning of the mouse obese gene and its human homologue. Nature 1994 1:372 (6505): 425-432. and as indicated in the UniProt database under accession number P41159 in the version of Aug. 24, 2021. In other embodiments the leptin is a pegylated (PEG)-leptin.

Preferably, the leptin analog is metreleptin, which is also a preferred leptin receptor agonist according to the invention.

The compounds of the invention can be administered as a "therapeutic composition", which can refer to any compounds administered to treat or prevent a disease or a symptom(s) thereof, such as complications associated with weight loss or underweight. For example, aspects of the invention are drawn towards uses of therapeutic compositions comprising leptin and/or leptin receptor agonists, such as metreleptin.

In embodiments, the therapeutic composition can comprise human recombinant leptin and derivatives or fragments thereof. For example, Metreleptin (Myalept®) is an FDA-approved treatment for generalized and familial dyslipidemia, and thus could readily be repurposed to treat or prevent the loss of the counter-regulatory response in diabetes patients. Thus, embodiments of the invention comprise treatment strategies for utilizing metreleptin to treat or prevent neuropsychiatric conditions associated with weight loss or underweight as disclosed herein.

One preferred leptin receptor agonist to be used in the context of the present invention is an antibody binding to the leptin receptor and having an agonistic effect on the leptin receptor. Such compounds are referred to herein as "anti-leptin receptor antibody" or "anti-LEPR antibody". The term "antibody", as used herein, means any antigen-binding molecule or molecular complex comprising at least one complementarity determining region (CDR) that specifically binds to or interacts with a particular antigen (e.g., leptin receptor). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-LEPR antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Leptin receptor antibodies are for example disclosed in WO/2019/195796, which is incorporated herein by reference in its entirety. A particular antibody preferred in context of the invention is REGN4461 of Regeneron®, which is currently in clinical trials for the treatment of Lipodystrophy. In WO/2019/195796 the antibody sequence and its derivatives or fragments, denoted as H4H174319P2 is particularly preferred. As such in certain embodiments an antibody binding the identical antigen of H4H174319P2 is preferred, and/or an antibody having the CDR1 to CDR3 sequences of both heavy and light chain of H4H174319P2 are preferred antibodies of the invention.

Compositions as utilized herein can also be provided as therapeutic or prophylactic combination compositions that comprise leptin, fragments thereof, and/or leptin receptor agonists, and one or more additional active agents. For example, a therapeutic or prophylactic combination composition can comprise leptin and an anti-depressant that can be used to prevent and/or treat anorexia nervosa and associated psychiatric conditions.

The therapeutic compositions can be incorporated into pharmaceutical compositions suitable for administration. Such compositions can comprise leptin, fragments thereof, and/or leptin receptor agonists, and a pharmaceutically acceptable carrier. Thus, in some embodiments, the compounds of the invention are present in a pharmaceutical composition. According to the invention, a pharmaceutically acceptable carrier can comprise any and all solvents, dispersion media, coatings, antibacterial and antifungal agents, isotonic and absorption delaying agents, and the like, compatible with pharmaceutical administration. Non-limiting examples of pharmaceutically acceptable carriers comprise solid or liquid fillers, diluents, and encapsulating substances, including but not limited to lactose, dextrose, sucrose, sorbitol, mannitol, xylitol, erythritol, maltitol, starches, gum acacia, alginate, gelatin, calcium phosphate, calcium silicate, cellulose, methyl cellulose, microcrystalline cellulose, polyvinylpyrrolidone, water, methyl benzoate, propyl benzoate, talc, magnesium stearate, and mineral oil. The use of such media and agents for pharmaceutically active substances is well known in the art. Any conventional media or agent that is compatible with the active compound can be used. Supplementary active compounds can also be incorporated into the compositions.

The term "therapeutically effective amount" can refer to those amounts that, when administered to a subject in view of the nature and severity of that subject's disease or condition, will have a desired therapeutic effect, e.g., an amount which will cure, prevent, inhibit, or at least partially arrest or partially prevent a target disease or condition. In some embodiments, the term "therapeutically effective amount" or "effective amount" can refer to an amount of a therapeutic agent that when administered alone or in combination with an additional therapeutic agent to a cell, tissue, or subject is effective to prevent or ameliorate the disease or condition such as a hypoglycemia-associated disease or condition or the progression of the disease or condition. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

A therapeutically effective dose can depend upon a number of factors known to those of ordinary skill in the art. The dose(s) can vary, for example, depending upon the identity, size, and condition of the subject or sample being treated, further depending upon the route by which the composition is to be administered, if applicable, and the effect which the practitioner desires. These amounts can be readily determined by the skilled artisan.

In some embodiments, the therapeutically effective amount is at least about 0.1 mg/kg body weight, at least about 0.25 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 3500 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight. The dosage can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion.

In further embodiments, metreleptin is administered at 0.06 mg/kg to 10 mg per day, once daily, preferably wherein metreleptin is administered at about 3 to 10 mg per day, once daily.

In accordance with some embodiments of the invention the leptin, or the leptin- and/or leptin receptor agonist, or the leptin analog or derivative thereof, is administered at: from about 1 microgram per day, from about 5 micrograms per day, about 10 micrograms per day, from about 50 micrograms per day, or from about 100 micrograms per day; to about 100 micrograms per day, to about 500 micrograms per day, to about 1 mg per day, to about 5 mgs per day, to about 50 mgs per day, or to about 100 mgs per day; or from about 0.01 mg per kilogram to about 0.3 mg, or from about 0.01 mg per kilogram to about 20 mgs per kilogram.

In preferred embodiments of the invention the metreleptin is administered at: from about 1 mg per day, from about 5 mgs per day, to about a maximum of 10 mgs per day; or from about 0.06 mg per kilogram per day to about 2.5 mgs per kilogram per day.

The term "administration" can refer to introducing a substance, such as leptin, fragments thereof, and/or leptin receptor agonists, or a composition comprising leptin, into a subject. Any route of administration may be utilized. Examples of routes of administration include parenteral, e.g., intravenous, intradermal, subcutaneous, oral, transdermal (topical), transmucosal, and rectal administration. In certain preferred embodiments the leptin, or the leptin- and/or leptin receptor agonist, or the leptin analog or derivative thereof, is administered once daily, or is administered in two or more dose administrations over one day, wherein the sum of doses administered does not exceed the daily dosage of metreleptin. Further included administration routes are oral or intranasal administration routes.

In embodiments, the leptin dose can be adjusted. For example, the leptin dose can be adjusted up or adjusted down. For example, the leptin dose can be adjusted up for a period of time, and then down for a period of time. In a clinical setting, for example, leptin can be administered at a dose of about 0.04 mg/kg/day for female patients and 0.02 mg/kg/day for male patients for the first four weeks and doubled after for an additional 16 weeks.

In further embodiments of the invention the administration of the leptin, or the leptin- and/or leptin receptor agonist, or the leptin analog or derivative thereof, is an administration of metreleptin or PEG-leptin (pegylated leptin) by subcutaneous injection.

The administration of a therapeutically effective amount of leptin, or the leptin agonist, analog or derivative thereof, to the subject so ameliorates in the subject one or more adverse conditions associated with the neuropsychiatric condition selected from the group consisting of hyperactivity/urge to move/inner restlessness, inner tension, preoccupation with food, rigid thinking, ruminations, obsessive thinking, compulsive acts, depressed mood/depression, reduced motivation to overcome the condition, reduced ability to concentrate, reduced social interaction, reduced insight into the neuropsychiatric disorder, reduced ability to cope with the disorder and respond to standard therapy, perception of bloating, bloating, fear of weight gain, underweight, loss of hunger and appetite, loss of libido (libido=sexual drive/desire for sexual activity), reduced hematopoiesis, starvation related physical appearance (e.g. brittle hair, reduced skin turgor), hair loss, and constipation.

A "subject" or "patient" in context of the invention is preferably a mammal such as a primate. Preferred subjects are human subjects and include a female (or male) human.

Preferred subject indicated for a treatment of the invention is a human and has a body mass index (BMI) of less than about 20 kg/m$^2$, 19.0 kg/m$^2$, preferably of less than 18.0 kg/m$^2$, 17.5 kg/m$^2$, 16.5 kg/m$^2$, or less than 15 kg/m$^2$, 14 kg/m$^2$, 13 kg/m$^2$, or less than 12 kg/m$^2$, 11 kg/m$^2$ or 10 kg/m$^2$.

In another embodiments of the invention the subject indicated for a treatment of the invention is a human patient and is distinguished by having a serum leptin concentration of about 5 ng/ml or less.

Human subjects indicated for the treatments of the invention are usually and subjects suffering from mild to severe depressive disorder and/or from mild to severe hyperactivity and/or mild to severe preoccupation with food and/or reduced hematopoiesis.

As such a subject is a human patient suffering from anorexia nervosa induced hypogonadotropic hypogonadism and wherein the administration of a therapeutically effective amount of the leptin, or the leptin- and/or leptin receptor agonist, or the leptin analog or derivative thereof, to the subject ameliorates in the subject hypogonadotropic hypogonadism, such as an increase/normalization in blood estrogen/testosterone levels and increase in libido.

In a second aspect, the invention pertains to a method for increasing body weight in a subject in need of the treatment, the method comprising a step of administering an effective amount of leptin, or a leptin- and/or leptin receptor agonist, or a leptin analog or derivative thereof, to the subject. For this aspect the above mentioned embodiments shall equally apply.

In context of the invention the subject suffers from one or more neuropsychiatric conditions that cause or increase weight loss or underweight, major depression, irrespective whether, mild, moderate or severe; and/or suffers from moderate or severe inner restlessness, hyperactivity or severe hyperactivity; and/or wherein the subject suffers from an eating disorder, such as preferably (typical) anorexia nervosa.

The terms "of the [present] invention", "in accordance with the invention", "according to the invention" and the like, as used herein are intended to refer to all aspects and embodiments of the invention described and/or claimed herein.

As used herein, the term "comprising" is to be construed as encompassing both "including" and "consisting of", both meanings being specifically intended, and hence individually disclosed embodiments in accordance with the present invention. Where used herein, "and/or" is to be taken as specific disclosure of each of the two specified features or components with or without the other. For example, "A and/or B" is to be taken as specific disclosure of each of (i) A, (ii) B and (iii) A and B, just as if each is set out individually herein. In the context of the present invention, the terms "about" and "approximately" denote an interval of accuracy that the person skilled in the art will understand to still ensure the technical effect of the feature in question. The term typically indicates deviation from the indicated numerical value by ±20%, ±15%, ±10%, and for example ±5%. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. As will be appreciated by the person of ordinary skill, the specific such deviation for a numerical value for a given technical effect will depend on the nature of the technical effect. For example, a natural or biological technical effect may generally have a larger such deviation than one for a man-made or engineering technical effect. Where an indefinite or definite article is used when referring to a singular noun, e.g. "a", "an" or "the", this includes a plural of that noun unless something else is specifically stated.

It is to be understood that application of the teachings of the present invention to a specific problem or environment, and the inclusion of variations of the present invention or additional features thereto (such as further aspects and embodiments), will be within the capabilities of one having ordinary skill in the art in light of the teachings contained herein.

Unless context dictates otherwise, the descriptions and definitions of the features set out above are not limited to any particular aspect or embodiment of the invention and apply equally to all aspects and embodiments which are described.

All references, patents, and publications cited herein are hereby incorporated by reference in their entirety.

EXAMPLES

Certain aspects and embodiments of the invention will now be illustrated by way of example and with reference to the description, figures and tables set out herein. Such examples of the methods, uses and other aspects of the present invention are representative only, and should not be taken to limit the scope of the present invention to only such representative examples.

The results are shown in Milos et al. 2020; Translational Psychiatry volume 10, Article number: 303 (2020), as well as in Antel, J., et al., Eur Child Adolesc Psychiatry (2021), both incorporated herein in their entirety.

The examples show:

Methods

Setup and Pre-Treatment Evaluation

Two adult female inpatients (A, B) were treated at the Eating Disorders Unit, University Hospital Zurich, Switzerland, an adolescent female inpatient (C) at the Department of Child and Adolescent Psychiatry in Essen, Germany. All three patients suffered from intermittently life-threatening AN diagnosed according to DSM-5 (Table 1). This illness severity was also experienced by the patients themselves and represented the overarching inclusion criterion for the off-label treatment. All three patients subjectively complained about their drive for activity; the clinically apparent hyperactivity was rated as pronounced by the treatment teams (see FIGS. 1 to 3).

For patient B, the local therapeutic team had considered palliative treatment after consultation with a clinical ethicist because of treatment refractory AN. The initiation of dosing was postponed twice due to somatic instability. One day prior to dosing, she was transferred back to the Eating Disorders Unit after a 2-week treatment in the internal medicine ward, including nasogastric feeding, to achieve a stable somatic condition. In light of pre-relapse underweight in patient A, patient C was additionally selected for premorbid obesity. She was intermittently transferred to Essen for a total of twelve days from a hospital in the region. To allow for pre- and post-treatment assessment the dosing period lasted six days only.

Weight gain represented a central goal of the inpatient treatment regimens prior, during and after metreleptin treatment. Patients were treated as usual in the two interdisciplinary and multimodal eating disorder treatment programs and were requested to follow a defined daily meal plan including a specified energy intake to achieve weight gain. All patients received three main courses and three interim meals per day with between 2700 and 3000 kcal/day.

During the entire observation periods including (i) pre-dosing, (ii) dosing, and (iii) follow-up, body weights of patients were not measured daily; weights clearly vacillated throughout. The inventors chose the closest weight measurements prior to and upon completion of dosing as body weights at T0 and T1 (see Table 2); an exception due to excessive drinking to "reduce appetite" was made for patient C, for whom the inventors used the realistic weight 2 days after end of dosing (d+2). Prior to dosing, only two patients (A: +5.8 kg, C: +10.9 kg) had gained weight (Tables 1 and 2); patient C had, however, vacillated between 42 and 44 kg in the 4 weeks prior to dosing 5 with a single peak at 45 kg due to water ingestion (see above).

TABLE 1

Descriptive case histories and clinical data of female patients
A-C with anorexia nervosa treated with metreleptin

| | | Patient | | |
|---|---|---|---|---|
| | | A | B | C |
| Type of AN (DSM-5) | | Restricting | Restricting | Binge-eating/ purging |
| Family history | | Maternal MDD and unspecified eating disorder | AN in maternal uncle | Paternal obesity |
| Previous AN hospitalizations | N | 1 | 5 | 4 |
| Age at referral | years | 26 | 19 | 17 |
| onset of AN | | 15 | 13 | 14 |
| menarche | | 15 | Primary amenorrhea | 12 |
| maximum lifetime weight* | | 14 | 15 | 14 |
| minimum weight during AN | | 26 | 17 | 16 |
| Weight at referral | kg | 30.0 | 34.0 | 32.5 |
| maximum lifetime** | | 45.0 | 42.0 | 97.0 |
| minimum during AN | | 30.0 | 30.7 | 32.5 |
| Height at referral | cm | 162 | 164 | 166 |
| BMI at | kg/m$^2$ | | | |
| referral | | 11. Apr | 12. Jun | 11. Aug |
| maximum lifetime*** | | 17. Jan | 15. Jun | 35.2 |
| minimum during AN | | 11. Apr | 11. Apr | 11. Aug |
| Metreleptin treatment | | | | |
| Dosing period | days | 9 | 14 | 6 |
| Doses**** | mg/day | 4-6-7.5-10-10-0-10-0-10 | 2-2-3-3-4.5-6-6-8-0-10-0-11.3-0-11.3 | 6-9-9-9-9-9 |
| Concurrent medication and daily doses | | Aripiprazole 10 mg, fluoxetine 60 mg, diazepam 5 mg*****, etilefrine hydrochloride 20 mg, multivitamin tablets with iron | Olanzapine 3-75 mg, sertraline 50 mg, phosphate 864 mg, multivitamin tablets | Olanzapine 2.5 mg, melperone 25 mg****** |
| Selection criteria for metreleptin treatment | | Severe hyperactivity experienced as agonizing and compulsive; MDD | Severe hyperactivity, MDD; palliative care considered in light of no weight gain after 12 weeks of current inpatient treatment episode including intermittent short-term medical stabilization in internal medicine unit | Severe hyperactivity, MDD, recurrent episodes of life-threatening hyponatremia due to excessive drinking of water; stagnation of weight gain during inpatient treatment; patient transferred from a neighboring hospital for |

TABLE 1-continued

| Descriptive case histories and clinical data of female patients A-C with anorexia nervosa treated with metreleptin | | |
|---|---|---|
| Patient | | |
| A | B | C |
| | | metreleptin treatment |

*Maximum body weight prior to metreleptin treatment
**Recalled body weight
***BMI calculated using current height
****Doses "0" indicates days during which treatment was discontinued
*****Diazepam discontinued by patient on day 4
******Physician consented discontinuation of melperone and olanzapine during metreleptin treatment (days 3 and 4)
AN: anorexia nervosa
BMI: body mass index
MDD: major depressive disorder

TABLE 2

| Safety, self- and clinician rated psychological data for patients A-C prior (T0) and at end of metreleptin treatment | | | | | | | |
|---|---|---|---|---|---|---|---|
| | | Patient | | | | | |
| | | A | | B | | C | |
| | | T0 | T1 | T0 | T1 | T0 | T1 |
| Safety data | | | | | | | |
| Body weight | kg | 35.6 | 37.2 | 34 | 33.4 | 42.9 | 42.7 |
| BMI | kg/m$^2$ | 13. Jun | 14. Feb | 12. Jun | 12. Apr | 15. Jun | 15. Mai |
| Pulse (range) | | 52-72 | 61-84 | 68-76 | 72-72 | 52-77 | 57-64 |
| Systolic/diastolic blood | mmHg | 85/55- | 85/55- | 90/65- | 80/60- | 75/60- | 100/60- |
| pressure (range) | | 90/70 | 95/60 | 95/60 | 90/60 | 113/58 | 105/70 |
| Body temperature (range) | ° C. | 36.2-37.1 | 36.1-37.3 | 35.2-36.0 | 35.6-36.8 | 36.5* | 35.8* |
| Serum glucose (range) | mmol/l | 4.6-5.1 | 5.1-6.5 | 3.8-4.3 | 4.8-5.1 | 4.8-6.2 | 4.1-6.6 |
| Leucocytes | /nl | Apr 59 | 06. Dez | 02. Jan | 03. Feb | Mrz 29 | Apr 74 |
| Lymphocytes | /nl | 0.73 | 0.91 | 0.83 | 01. Jun | 0.7 | Jan 38 |
| Erythrocytes | /nl | Mrz 38 | Mrz 63 | Mrz 27 | Mrz 29 | Apr 48 | Apr 71 |
| Thrombocytes | /nl | 235 | 266 | 231 | 208 | 247 | 192 |
| GOT | U/l | 25 | 35 | 38 | 32 | 22 | 34 |
| GPT | U/l | 13 | 43 | 60 | 28 | 44 | 47 |
| Amylase | U/l | 70 | 68 | 44 | 53 | 54 | 69 |
| Lipase | U/l | 71 | 72 | 63 | 86 | 46 | 64 |
| Electrocardio-gram | | Sinus | Sinus | Sinus | Sinus | Sinus | Sinus |
| | | rhythmNAD | rhythm NAD | rhythm NAD | rhythm NAD | bradycardia; NAD | bradycardia; NAD |
| Self-ratings | | | | | | | |
| BDI-II | | 34 | 15 | 37 | 27 | 37 | 6 |
| EDI-2 | Percentile rank | | | | | | |
| | Total score | 84 | 87 | 87 | 87 | 99 | 80 |
| | Drive for Thinness | 75 | 75 | 85 | 90 | 99 | 75 |
| | Bulimia | 1 | 99 | 1 | 1 | 99 | 45 |
| | Body Dissatisfaction | 45 | 10 | 55 | 55 | 95 | 75 |
| | Ineffectiveness | 99 | 85 | 95 | 95 | 99 | 80 |
| | Perfectionism | 75 | 10 | 70 | 70 | 90 | 70 |
| | Interpersonal Distrust | 95 | 55 | 80 | 85 | 60 | 50 |
| | Interoceptive Awareness | 65 | 99 | 95 | 90 | 99 | 85 |
| | Maturity Fears | 40 | 90 | 70 | 80 | 99 | 99 |
| Clinician ratings | | | | | | | |
| HAMD-17 | | 29 | 12 | 22 | 15 | 31 | 14 |
| Leptin serum levels** | | | | | | | |
| T0 | ng/ml | <0.5 | | <0.5 | | <0.1 | |
| | | | | | | 3 time points: | |
| During treatment | ng/ml | 72.9 | | 04. Apr | | 06. Jul | 55.9 | 80.8 |
| Treatment day | | 7 | | 13 | | 2 | 4 | 5 |
| Last dose | mg | 10 | | 11. Mrz | | 6 | 9 | 9 |

TABLE 2-continued

| | | | | | | | |
|---|---|---|---|---|---|---|---|
| Safety, self- and clinician rated psychological data for patients A-C prior (T0) and at end of metreleptin treatment | | | | | | | |
| | | | Patient | | | | |
| | | A | | B | | C | |
| | T0 | T1 | T0 | T1 | T0 | | T1 |
| Hours after sc. application*** | 7 | | 22 | | 22 | 2 | 4 |

NAD: No abnormality detected
BDI-II: Beck Depression Inventory-II
BMI: body mass index
EDI-2: Eating Disorder Inventory-2
HAMD-17: Hamilton Depression Scale-17
s.c.: subcutaneous
*measured once daily only
**assays performed in Zurich (A, B) and Essen (C)
***for metreleptin a half-life of 3.8-4.7 h and a median tmax of 4 h (range 2-6 h) following s.c. administration was reported in patients with lipodystrophy12

Clinical Assessment

All patients filled in a 10-item visual analogue scale (VAS; scaled 1-10) twice or thrice daily (FIG. 1). All patients were additionally assessed with the Hamilton Depression Scale-17[21] (HAMD-17) by non-blinded clinical raters. Self-rating scales included Eating Disorders Inventory-2[22] (EDI-2) and Beck Depression Inventory-II (BDI-II)[23]. Patients were clinically monitored during treatment (Table 2).

Treatment

Metreleptin was applied subcutaneously (thigh) once daily at 9:30 am; dosage recommendations for patients with lipodystrophy served as guidance12. In patient A, the maximum dosage of ten mg was reached at day 4 four (Table 1). For patient B, who was the most acutely ill patient with the lowest body mass index (BMI) at baseline, the dosage was slowly titrated for safety concerns; she received the highest dosage of 11.3 mg on days twelve and fourteen. Based on the observed, uncomplicated courses of patients A and B, patient C was titrated to the maximal dose of nine 9 mg at day two. Metreleptin was intermittently discontinued in patients A and B (Table 2).

Example 1: Primary Treatment Results

Figure 2:
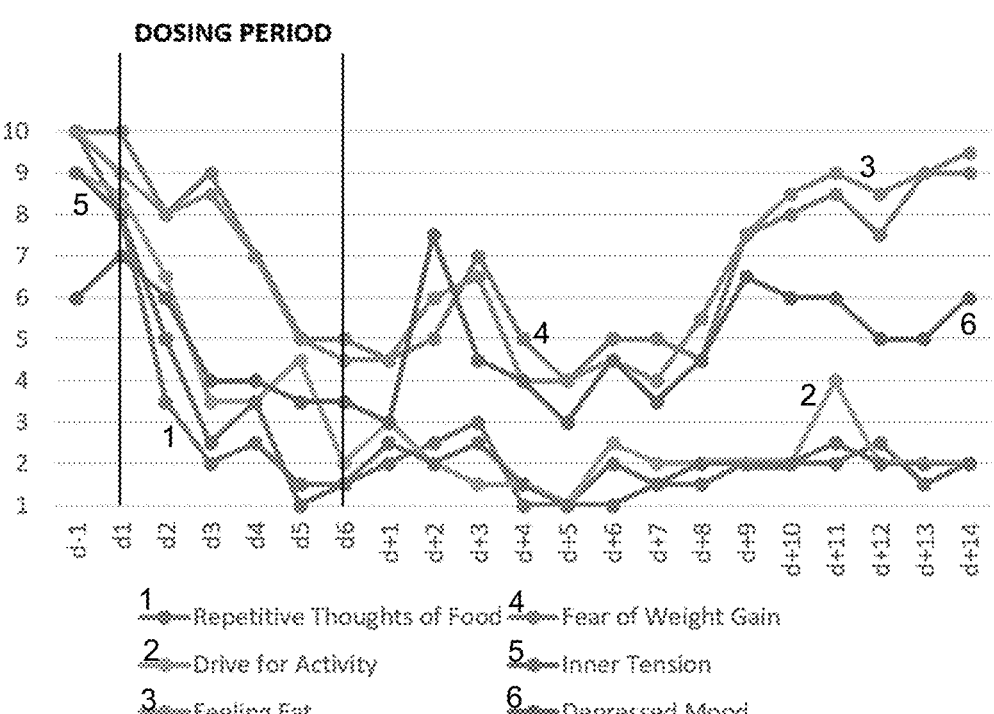
FIG. 2: shows VAS for key cognitions and emotions: Effects of short-term metreleptin treatment in patient C including follow-up observations for 14-days, showing means of (patient self-rated) six key cognitions and emotions assessed twice daily with visual analog scales (range 1-10).
Figure 3:
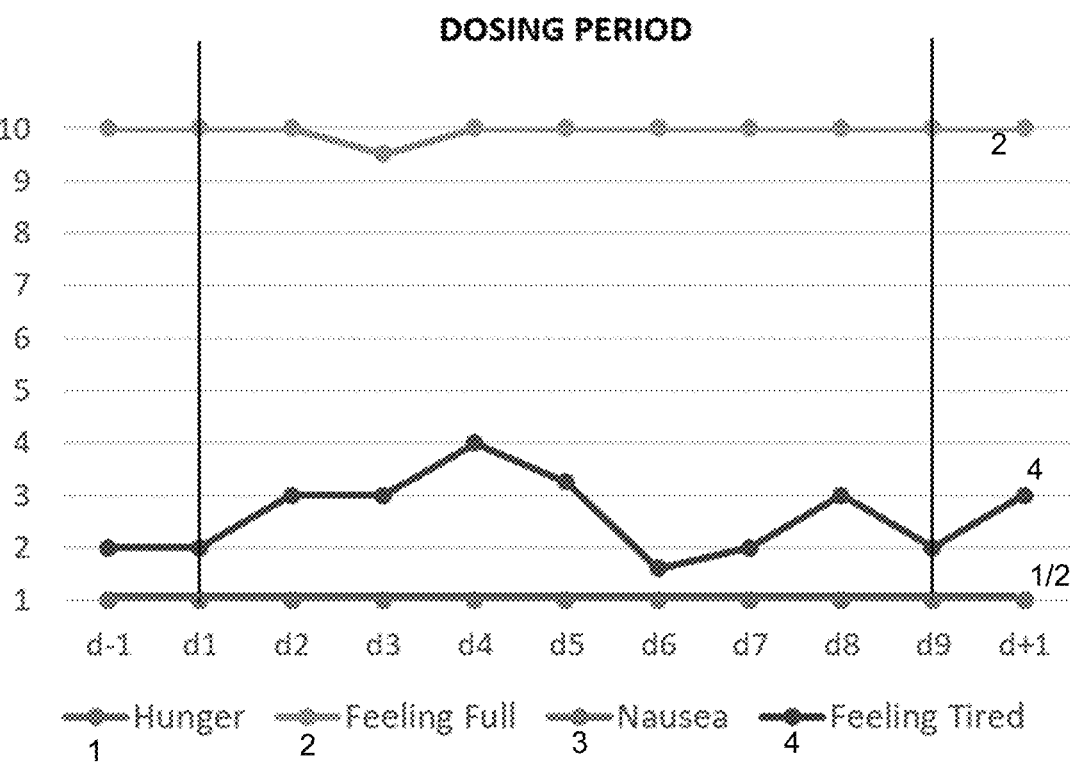
FIG. 3: shows VAS for safety and physiology: Effects of short-term metreleptin treatment on four self-ranked safety/physiological parameters in patient A assessed thrice daily with visual analog scales (range 1-10).
Figure 4:
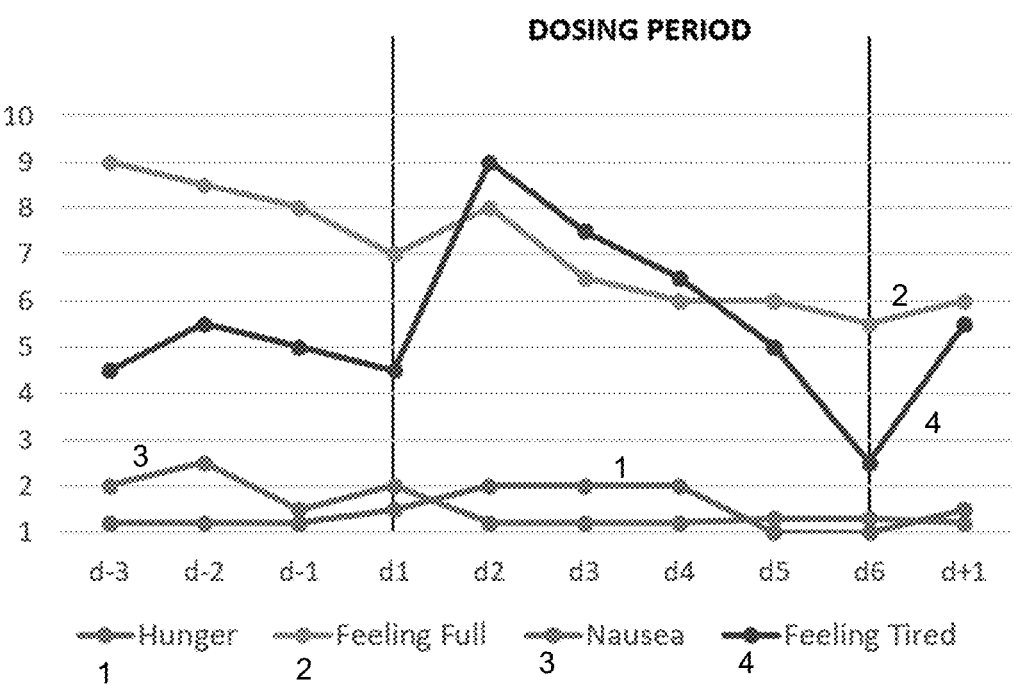
FIG. 4: shows VAS for safety and physiology: Effects of short-term metreleptin treatment on four self-ranked safety/physiological parameters in patient C assessed twice daily with visual analog scales (range 1-10).

Two days after initiation of dosing, patients A and C began to rank most VAS items for key cognitions and emotions as less severe (FIGS. 1 and 2). In the following days, the downward trend continued towards a plateau with low values. Both patients reported a more "realistic" assessment of body shape and weight. Patient B reported no changes (data not shown). Self-rated (VAS; FIGS. 3 and 4) safety/physiological items were not affected systematically.

During dosing periods, patient A gained 1.6 kg, patients B and C lost 600 and 200 grams (Table 2); hunger was continuously rated as (almost) absent (FIG. 4). Fear of gaining weight, which was initially rated maximal by patient A, decreased during dosing (FIG. 1). Despite low hunger ratings (FIG. 2), patient C reported an increase in "appetite" during treatment, which upset her in light of previous episodes of binge eating. Depressed mood, inner tension and drive for activity increased in patient A during the 14 day long post-dosing observation period; fear of weight gain did not rebound. In patient C fear of weight gain and feeling fat rebounded (FIG. 2).

Self-rated depressive symptoms (BDI-II) decreased in all patients with patients A and especially C showing substantially lower values (Table 2). While the total EDI-2 score improved only in patient C the clinician-rated HAMD-17 revealed reductions in depressive symptoms in all patients.

Circulating leptin levels, which were initially in the range characteristic for patients with acute AN4, reached high levels two to seven hours after metreleptin application, and were in the low normal range in the morning prior to the next dosing. Increments were observed for leucocytes and lymphocytes in all patients. Pulse, blood pressure, body temperature, blood glucose and other laboratory parameters revealed no systematic changes (Table 2).

Serious adverse events were not observed. In patient A, the upswing in mood was so pronounced, that dosing was discontinued on two days (Table 1). The patient herself reported a "happiness" equivalent to her lifetime maxima. She stopped taking diazepam because she no longer dreaded meals; she was surprised by the fact that she was able to phone lying relaxed in bed. Patient C experienced extended night sleeps and naps, which she experienced as healthy. Accordingly, treatment with melperone and olanzapine was terminated at days 3 three and 4four, respectively.

Six months after treatment, patient A had achieved her lifetime maximal BMI of 20 kg/m$^2$; her menses had resumed; she was well integrated in everyday life. She had intermittently developed panic attacks and a temporary episode of major depression, both of which had also occurred prior to referral. Patients B and C were discharged at days +33 and +24 due to failure to gain weight with BMIs of 12.4 kg/m$^2$ and 15.9 kg/m$^2$. Both are currently being treated on an outpatient basis.

Example 2: Additional Clinical Observations

Clinical observations by treatment teams revealed: a slight and substantially decreased of hyperactivity in patient B and patients A and C, respectively. Both explained that metreleptin treatment allowed them to think outside the "cage" meaning that they were able to view themselves "realistically" without being constrained by their eating disorder. Both reported a substantial boost in their motivation to overcome AN, which patient A, but not patient C, was able to act upon. During dosing, patient C reported being able to discern her emotions more readily; prior to dosing she had been overwhelmed by them. According to her parents, she was substantially less hyperactive and agitated, her mood improved. She reported on dream contents unrelated to food.

All patients reported an improved ability to concentrate. They more readily initiated personal contacts, e.g. a renewed desire to contact friends and relatives (patient A), playing board games with other patients (B) and an intense, but fruitful, discussion with her parents (C).

Patient A reported less constipation. In patients A and C, the skin prior to subcutaneous application of metreleptin appeared wrinkly and dry. It rapidly normalized in turgor during dosing. Patient C observed healing and initial hair growth in bald spots due to excessive scratching.

Metreleptin dosing induced similar and strong cognitive, emotional, and behavioral effects in two patients. After cessation most variables rebounded which suggests that hypoleptinemia may contribute to the characteristic clinical symptomatology of AN. Notably, less pronounced beneficial effects were also observed in patient C. Only patient A was able to gain weight during treatment; the weight losses (200 and 600 grams) in the other two patients may reflect an effect of metreleptin. However, both the pre- and post-dosage weight courses also reflect vacillations and stagnation of weight gain.

The inventors had hypothesized to observe beneficial effects on hyperactivity and starvation related emotions/ cognitions, but were surprised by the rapid onset, the multiplicity of effects, the apparent effect sizes and the decrease in AN specific cognitions such as fear of weight gain and feeling fat. These effects seemingly allowed the patients an intermittent escape from the 'golden cage'[24] of their eating disorder.

The somatic observations merit discussion. Increments in blood cell counts may reflect hematopoetic effects of leptin[25]. In the skin, leptin has been linked to cell differentiation, proliferation, migration and survival with pronounced effects on angiogenesis, blood flow and tissue perfusion, thus affecting skin aging, wound healing and hair follicle morphogenesis[26]. Leptin also functions as an important modulator of gastrointestinal tract functions[27].

This small case series was set up to potentially help the patients and secondly to support the biomedical hypotheses[3]. The individualized dosing schemes were based on safety considerations and ad hoc clinical observations. For regulatory and ethical reasons the inventors were unable to consider matched, placebo treated controls. This limitation entails that some of the observed improvements may represent treatment expectation (placebo) effects: Other limitations are individual dosing schemes and concurrent medications.

While the decreased hyperactivity supported the primary hypothesis in the present uncontrolled case series, the compelling and rapid changes of cognitive, emotional, and behavioral symptoms clearly warrant adequately powered randomized, double blind placebo controlled clinical trials (RCTs).

Important questions relate to treatment duration, minimal effective dose and medium-term safety. Patients might have profited from longer treatment durations. During dosing, patients A and C seemed much more amenable to psychotherapy due to their elevated motivation and detachment from eating disordered cognitions. It remains to be seen to what extent the clinical changes enable longer-term behavioral changes and importantly weight gain. Whereas metreleptin had an effect on hyperactivity potentially by reducing inner tension and drive for activity, a short-term effect on energy intake was not as evident. All of the patients had been ill for extended time periods entailing the need to rapidly adapt to the induced changes; severity of starvation, premorbid body-weight (Table 1), and/or type of AN may account for short- and medium-term response variation. RCTs are required to assess whether a) patients with shorter illness duration and less severe symptomatology may profit more, and b) for how long "the cage needs to be unlocked" to allow patients—supported by standard treatment regimens—a more permanent 'escape' brought on by a positive energy balance, subsequent weight gain and the resumption of a sufficient endogenous leptin secretion. These results indirectly support weight rehabilitation as the mainstay of AN treatment[3].

Replication provided, AN may be recognized in part as a hormone deficiency syndrome. Hormones influence both cognitions and emotions with timing effects and critical periods[28]. The strong female preponderance of AN and the typical manifestation during the second decade of life may suggest such a sex-specific critical period. The seemingly different pathways, through which hypoleptinemia evokes emotional, cognitive, and behavioral derangements, need to be deciphered. In mice, leptin suppresses the rewarding effects of running via activation of signal transducer and activator of transcription-3 signaling in dopaminergic neurons of the ventral tegmental area without simultaneously affecting the anorectic actions of leptin and hedonic and compulsive feeding behavior[7]. The temporary evolution of specific cognitions, emotions, and behaviors during and after metreleptin treatment may help to elucidate if and how they are inter-related in patients.

Example 3: Metreleptin Treatment in a Male Adolescent Anorexia Nervosa Patient Fifteen year old F initially presented with a BMI of 14.1 kg/m2 (<1st BMI sex- and age-matched percentile) after a rapid weight loss of 12 kg within 2.5 months (premorbid BMI 18.1 kg/m2) fulfilling DSM-5 diagnostic criteria for the restricting type of AN; F skipped meals and replaced regular 'unhealthy' food with fruits and vegetables. Mood and liveliness had deteriorated over the last six months. F had been active in team sports but had increasingly resorted to daily endurance training. F's weight as a child had been above average (annual documentation of measured height and weight between ages 0 to 5; BMI percentiles between 61 and 81; photos during later childhood suggest overweight). His protruding belly had been of concern to him from the age of seven years on; upon referral he perceived himself as chubby. During his first inpatient treatment of two months duration F gained nine kg to be discharged at 52.2 kg (17.0 kg/m2). Due to instable mood, persistent inner tension, restrictive eating and renewed weight loss (50.5 kg) he was readmitted after only two weeks. After seven weeks F dis-charged himself (57 kg); a pronounced body image disturbance persisted. After only ten days he sought renewed admission (53.7 kg) due to suicidal ideation and excessive hyperactivity. The clinical situation nevertheless deteriorated substantially and was characterized by stagnation of weight gain (oscillating around 52 kg; Suppl. Table 1), severe hyperactivity, depression and AN specific cognitions and manipulative behavior. Repeated episodes of hyperactivity lasted 2-4 days in form of brisk walking during the entire day (up to 70,000 steps/d; see "Methods" section) within a secured inner courtyard in addition to compulsive exercise conducted in his room and bathroom (self-reported 2000 jumping jacks and 200 push-ups daily). Such episodes were followed by two days of total exhaustion and severe depression, during which he remained in bed. On two occasions he threatened to commit suicide by jumping from a bridge entailing large scaled police searches; upon the second time he also conveyed extortion demands to be met by parents and treatment team to circumvent weight gain and therapeutic restrictions.

Treatment and Methods

Metreleptin dosages of 3-9 mg/d (3 mg: d1-d2, d4, d8, d13-d20, d22, d24; 6 mg: d3, d5-d7, d11-d12; 9 mg: d9-d10) were applied subcutaneously once daily at 9:30 am. The dosage was tapered prior to discontinuation (no dosing on d21 and d23). Concurrent medication to reduce hyperactivity included diazepam up to 2.25 mg between baseline and d4 and again from dg to d17. Olanzapine (3 mg/d) was discontinued after d3. Nasogastric feeding was pursued throughout the dosing period with F sometimes additionally eating food orally.

Figure 7:
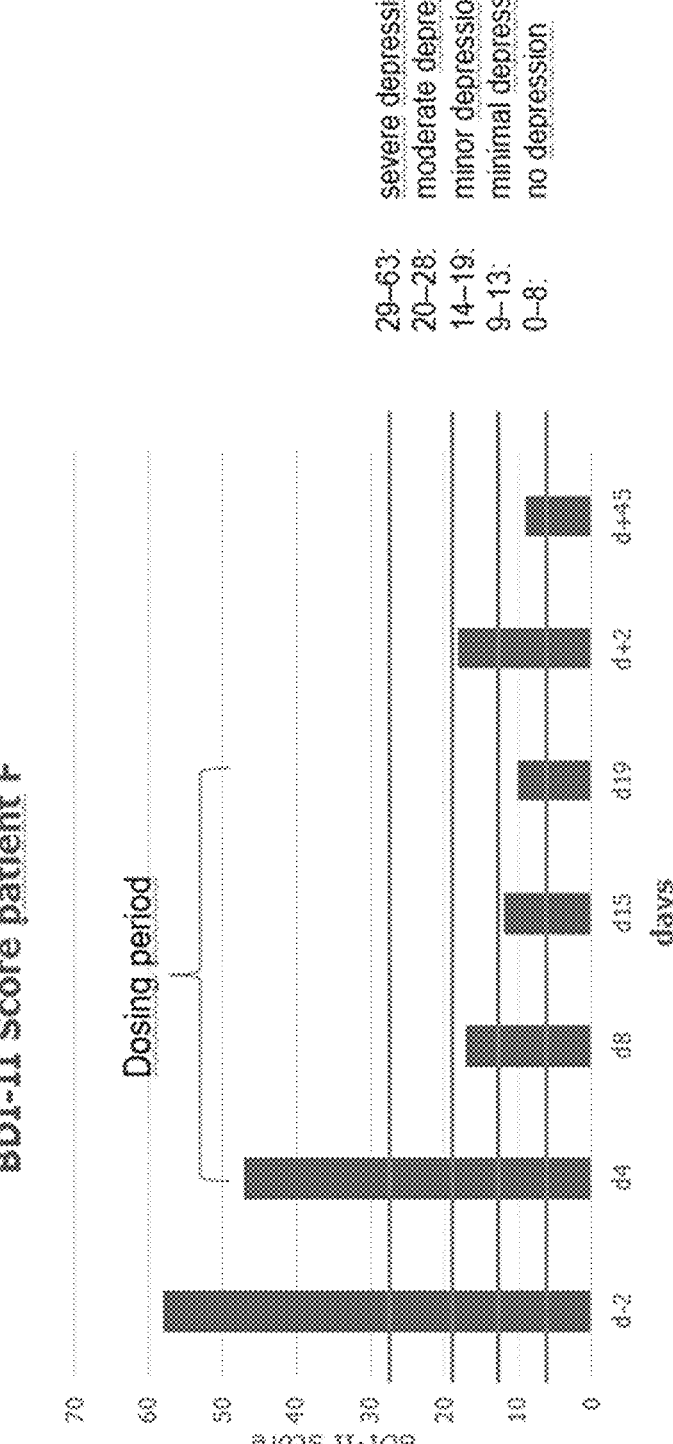
FIG. 7: shows self-reported BDI-II scores [Beck Depression Inventary II; Beck A T, Steer R A (1987) Beck depression inventory-manual. The Psychological Corporation, San Antonio] measured from two days prior to onset of treatment (d−2) up to 45 days after end of dosing (d+45) in the follow-up period.

As above and further routine and endocrine (free and total triiodothyronine (fT3, TT3), free and total thyroxine (fT4, TT4), thyroid stimulating hormone (TSH), (bioavailable) testosterone, follicle stimulating hormone (FSH), luteinizing hormone (LH), prolactin, insulin, C-peptide, and leptin, for which composite (leptin and metreleptin) diurnal profiles were obtained two times following application of 3 mg (d22) and 6 mg (d11) of metreleptin, respectively) were measured repeatedly Results Visual analogue scales (VAS), validated self- and clinician rating scales and lab results tracked changes from baseline to end of the 24-day dosing period and a five-month follow-up. Substantial improvements of mood and eating disorder related cognitions and hyperactivity set in after two days of treatment. The results therefore correspond to the observations of the examples 1 and 2. Further results are provided in FIG. 7.

Figure 5:
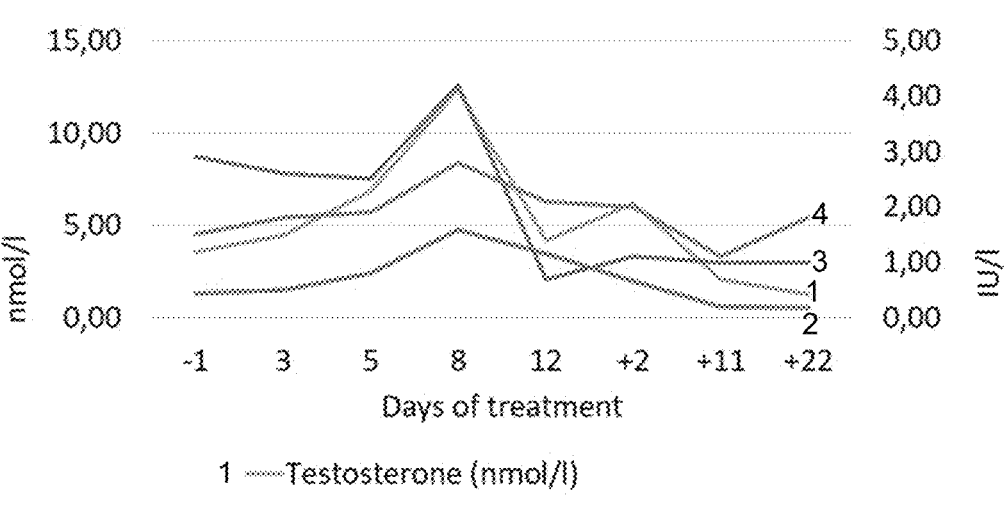
FIG. 5: shows hormone levels of the pituitary-gonadal axis prior to, during and after the 24-day dosing period (normal ranges: testosterone: 5.0-29.2 nmol/l; LH: 1.0-7.IU/l; FSH: 1.4-7.5 IU/1).
Figure 6:
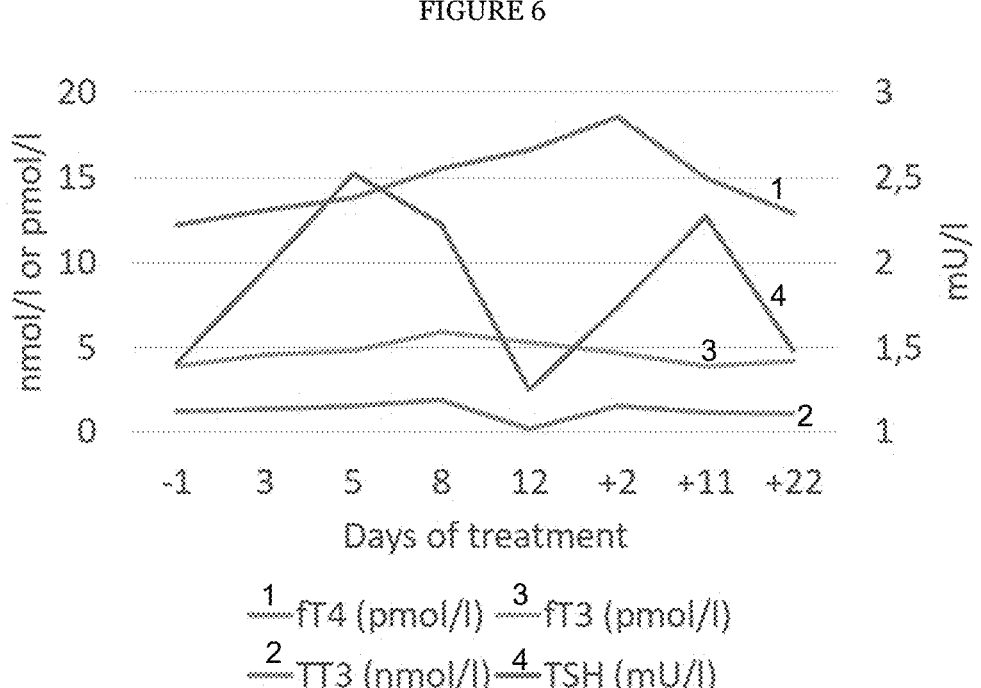
FIG. 6: shows hormone levels of the pituitary-thyroid axis prior to, during and after the 24-day dosing period (normal ranges: ft3: 4.2-7.47 pmol/l; ft4: 10.57-22.62 pmol/l; TT3: 1.31-2.9 pmol/l; TSH: 0.48-4.17 mU/l).

In addition, F proudly talked about three female patients who wished him to contact them at d13. F explained that an interest in sex had returned and voiced concerns that it would again disappear after end of dosing. In line with the reemergence of libido, he no longer scored in the BDI-II item 'loss of interest in sex' (drop from 3 to 0 between d8 and d15). At baseline, the patient presented with hypogonadotropic hypogonadism with marked testosterone deficiency. During treatment, testosterone levels rapidly normalized (FIG. 5). Concomitant to dose reduction to 3 mg/d as of d13 testosterone concentration fell to baseline levels. Changes of the pituitary-thyroid-axis also occurred (FIG. 6). Initially, the patient showed the typical constellation of non-thyroidal illness with low levels of fT3/TT3 and TT4 with inadequately normal TSH. Transient normalization of thyroid hormones occurred during dosing.

Figure 8:
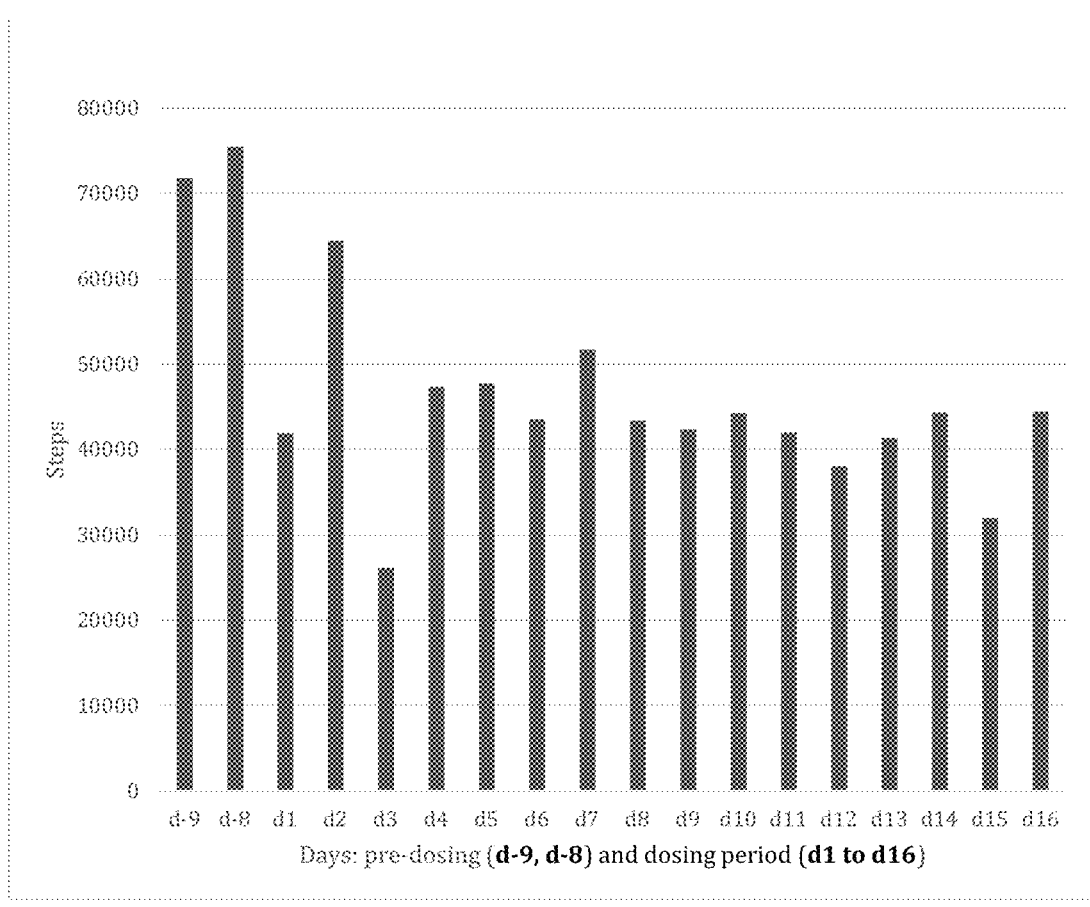
FIG. 8: shows step counts as measured with accelerometer (ActiGraph®). Data not to be taken at face value due to intermediate non-adherence (time protocols for wearing of accelerometer incomplete); prior to dosing patient experienced waxing and waning of both hyperactivity (e.g. d-9/d-8) and daytime bedrest (d-2/d-1). During dosing daily step counts were similar; days spent in bed did not reoccur. Accelerometry was discontinued at d17.

Reduced activity is quantified by step count during treatment and results are shown in FIG. 8.

REFERENCES

The References are:
1. [APA] APA. Diagnostic and Statistical Manual of Mental Disorders, 5th Edn. Arlington, V A: American Psychiatric Publishing; 2013.
2. Hebebrand J, Bulik C M. Critical appraisal of the provisional DSM-5 criteria for anorexia nervosa and an alternative proposal. Int.J Eat Disord 2011; 44:665-78.
3. Hebebrand J, Milos G, Wabitsch M, et al. Clinical Trials Required to Assess Potential Benefits and Side Effects of Treatment of Patients With Anorexia Nervosa With Recombinant Human Leptin. Front Psychol 2019; 10:769.
4. Hebebrand J, Blum W F, Barth N, et al. Leptin levels in patients with anorexia nervosa are reduced in the acute stage and elevated upon short-term weight restoration. Mol Psychiatry 1997; 2:330-4.
5. Ahima R S, Flier J S. Leptin. Annu Rev Physiol 2000; 62:413-37.
6. Exner C, Hebebrand J, Remschmidt H, et al. Leptin suppresses semi-starvation induced hyperactivity in rats: implications for anorexia nervosa. Mol Psychiatry 2000; 5:476-81.
7. Fernandes M F, Matthys D, Hryhorczuk C, et al. Leptin Suppresses the Rewarding Effects of Running via STAT3 Signaling in Dopamine Neurons. Cell Metab 2015; 22:741-9.
8. Coccurello R, Maccarrone M. Hedonic Eating and the "Delicious Circle": From Lipid-Derived Mediators to Brain Dopamine and Back. Front Neurosci 2018; 12:271.
9. Monteleone A M, Castellini G, Volpe U, et al. Neuroendocrinology and brain imaging of reward in eating disorders: A possible key to the treatment of anorexia nervosa and bulimia nervosa. Prog Neuropsychopharmacol Biol Psychiatry 2018; 80:132-42.
10. Khanh D V, Choi Y H, Moh S H, Kinyua A W, Kim K W. Leptin and insulin signaling in dopaminergic neurons: relationship between energy balance and reward system. Front Psychol 2014; 5:846.
11. Brown R J, Oral E A, Cochran E, et al. Long-term effectiveness and safety of metreleptin in the treatment of patients with generalized lipodystrophy. Endocrine 2018; 60:479-89.
12. FDA. SUMMARY REVIEW for Regulatory Action; Myalept; Application Number 125390Orig1s000, ed. C.F.D.E.A. RESEARCH. In: Administration FaD, ed. Silver Spring, M D: FDA; 2014.
13. Farooqi I S, Jebb S A, Langmack G, et al. Effects of recombinant leptin therapy in a child with congenital leptin deficiency. N Engl J Med 1999; 341:879-84.
14. Wabitsch M, Funcke J B, Lennerz B, et al. Biologically inactive leptin and early-onset extreme obesity. N Engl J Med 2015; 372:48-54.
15. Paz-Filho G, Wong M L, Licinio J. Ten years of leptin replacement therapy. Obes Rev 2011; 12: e315-23.
16. Welt C K, Chan J L, Bullen J, et al. Recombinant human leptin in women with hypothalamic amenorrhea. N Engl J Med 2004; 351:987-97.
17. Chou S H, Chamberland J P, Liu X, et al. Leptin is an effective treatment for hypothalamic amenorrhea. Proc Natl Acad Sci USA 2011; 108:6585-90.
18. Sienkiewicz E, Magkos F, Aronis K N, et al. Long-term metreleptin treatment increases bone mineral density and content at the lumbar spine of lean hypoleptinemic women. Metabolism 2011; 60:1211-21.
19. Parsa-Parsi R, Blackmer J, Ehni H J, Janbu T, Kloiber O, Wiesing U. Reconsidering the Declaration of Helsinki. Lancet 2013; 382:1246-7.
20. WMA. WMA Declaration of Helsinki-Ethical Principles for Medical Research Involving Human Subjects. Fortaleza, Brazil: 64th WMA General Assembly; 2013.
21. Hamilton M. A rating scale for depression. J Neurol Neurosurg Psychiatry 1960; 23:56-62.
22. Garner D M. Eating Disorder Inventory-2: Professional manual. Odessa, F L: Psychological Assessment Resources; 1991.
23. Beck A T, Steer R A, eds. Beck Depression Inventory-Manual. San Antonio: The Psychological Corporation1987.
24. Bruch H. The Golden Cage. The Enigma of Anorexia Nervosa, With a New Foreword by Catherine Steiner-Adair, Ed.D. Boston: Harvard University Press; 2001.

25. Fantuzzi G, Faggioni R. Leptin in the regulation of immunity, inflammation, and hematopoiesis. J Leukoc Biol 2000; 68:437-46.

26. Poeggeler B, Schulz C, Pappolla M A, et al. Leptin and the skin: a new frontier, Exp Dermatol 2010; 19:12-8.

27. Yarandi S S, Hebbar G, Sauer C G, Cole C R, Ziegler T R. Diverse roles of leptin in the gastrointestinal tract: modulation of motility, absorption, growth, and inflammation. Nutrition 2011; 27:269-75.

28. Auyeung B, Lombardo M V, Baron-Cohen S. Prenatal and postnatal hormone effects on the human brain and cognition. Pflugers Arch 2013; 465:557-71.

The invention claimed is:

1. A method for treating a neuropsychiatric symptom of anorexia nervosa in a human subject, the method comprising administering a therapeutically effective amount of leptin, a leptin- and/or leptin receptor agonist, a leptin analog or a derivative thereof, to the human subject suffering from anorexia nervosa, thereby ameliorating the neuropsychiatric symptom of anorexia nervosa in the human subject.

2. The method of claim 1, wherein the leptin, the leptin- and/or leptin receptor agonist, the leptin analog or the derivative thereof, is administered at: from about 1 microgram per day to about 100 mgs per day; or from about 0.01 mg per kilogram to about 20 mgs per kilogram.

3. The method of claim 1, wherein the leptin analog is metreleptin.

4. The method of claim 3, wherein the metreleptin is administered at: from about 1 mg per day, from about 5 mgs per day, to about a maximum of 10 mgs per day; or from about 0.06 mg per kilogram per day to about 2.5 mgs per kilogram per day.

5. The method of claim 4, wherein the metreleptin is administered once daily, or is administered in two or more dose administrations over one day, wherein the sum of doses administered does not exceed a daily dosage of metreleptin.

6. The method of claim 3, wherein the metreleptin is administered at 0.06 mg/kg to 10 mg/kg per day, once daily.

7. The method of claim 1, wherein the administration of the leptin, the leptin- and/or leptin receptor agonist, the leptin analog or the derivative thereof, is an administration of metreleptin, another type of human recombinant leptin, or PEG-leptin (pegylated leptin) by subcutaneous injection.

8. The method of claim 1, wherein the neuropsychiatric symptom of anorexia nervosa is one or more selected from the group consisting of urge to move, inner restlessness, inner tension, preoccupation with food, rigid thinking, ruminations, obsessive thinking, compulsive acts, depressed mood, depression, absent or reduced motivation to overcome the condition, reduced ability to concentrate, reduced social interaction, reduced insight into the neuropsychiatric disorder, reduced ability to cope with the disorder and respond to standard therapy, perception of bloating, fear of weight gain, and loss of libido.

9. The method of claim 1, wherein the human subject has a body mass index (BMI) of less than about 20 kg/m$^2$, less than 19.0 kg/m$^2$, less than 18.0 kg/m$^2$, less than 17.5 kg/m$^2$, less than 16.5 kg/m$^2$, less than 15 kg/m$^2$, less than 14 kg/m$^2$, less than 13 kg/m$^2$, less than 12 kg/m$^2$, less than 11 kg/m$^2$ or less than 10 kg/m$^2$.

10. The method of claim 1, wherein the human subject has a serum leptin concentration of about 5 ng/ml or less.

11. The method of claim 1, wherein the human subject further suffers from at least one selected from the group consisting of hyperactivity, constipation, bloating, hair loss, loss of appetite, underweight, and reduced hematopoiesis.

12. The method of claim 1, wherein the human subject further suffers from anorexia nervosa induced hypogonadotropic hypogonadism.

13. The method of claim 1, wherein the neuropsychiatric symptom of anorexia nervosa is one or more selected from the group consisting of fear of gaining weight, body image distortion, desire to be thin, and preoccupation with food and body weight.

14. The method of claim 1, further comprising providing psychotherapy to the human subject.

15. The method of claim 1, wherein ameliorating the neuropsychiatric symptom of anorexia nervosa facilitates weight gain in the human subject.

* * * * *